United States Patent [19]

Scardera et al.

[11] 4,337,168
[45] Jun. 29, 1982

[54] ALKOXYSILANE CLUSTER EMULSIONS AND THEIR PREPARATION

[75] Inventors: Michael Scardera, Hamden; Alan Norwid, Ansonia, both of Conn.

[73] Assignee: Olin Corporation, New Haven, Conn.

[21] Appl. No.: 300,836

[22] Filed: Sep. 10, 1981

[51] Int. Cl.³ .............................................. B01J 13/00
[52] U.S. Cl. .................................................... 252/312
[58] Field of Search ......................................... 252/312

[56] References Cited

U.S. PATENT DOCUMENTS

| | | | |
|---|---|---|---|
| 3,965,136 | 6/1976 | Knollmueller | 24/205.14 R |
| 4,077,993 | 3/1978 | Knollmueller | 556/451 |
| 4,160,776 | 7/1979 | Scardera et al. | 556/446 |
| 4,194,988 | 3/1980 | Schneider et al. | 252/312 |

Primary Examiner—Paul F. Shaver
Attorney, Agent, or Firm—William A. Simons; Thomas P. O'Day

[57] ABSTRACT

Disclosed is a stable emulsion system which comprises:
(a) an aqueous phase comprising water;
(b) an organic phase comprising tris(tri-sec-butoxysiloxy)methylsilane; and
(c) a surfactant having the formula:

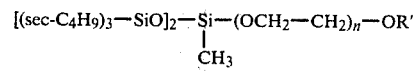

wherein n is from about 8 to about 16 and R' is either a methyl or ethyl group.

10 Claims, No Drawings

ALKOXYSILANE CLUSTER EMULSIONS AND THEIR PREPARATION

BACKGROUND OF THE INVENTION

1. Field of the Invention

This invention relates to a stable emulsion of water and tris(tri-sec-butoxysiloxy)methylsilane using certain silicate ethylene oxide adducts as surfactants to effect such emulsions.

2. Description of the Prior Art

Alkoxysilane cluster compounds, and particularly tris(tri-sec-butoxysiloxy)methylsilane, are disclosed in U.S. Pat. No. 3,965,136, which issued to Karl Knollmueller on June 22, 1976. These compounds have been disclosed to be very good functional fluids.

Repeated attempts to form aqueous emulsions with alkoxysilane compounds such as tris(tri-sec-butoxysiloxy)methylsilane using conventional surfactants did not result in stable systems. It would be advantageous to make alkoxysilane cluster emulsions since they may be used in a wide variety of applications, such as in waxes and polishes (e.g., the floors, furniture, automobiles, and the like).

Accordingly, there is a need in the art for a suitable surfactant to make emulsions with alkoxysilane cluster compounds such as tris(tri-sec-butoxysiloxy)methylsilane. The present invention gives a solution to that need.

BRIEF SUMMARY OF THE INVENTION

The present invention, therefore, is directed to a stable emulsion system (oil-in-water) which comprises:
(a) an aqueous phase comprising water;
(b) an organic phase comprising tris(tri-sec-butoxysiloxy)methylsilane; and
(c) a surfactant having the formula:

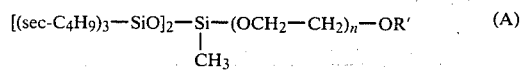

wherein n is from about 8 to about 16 and R' is either a methyl or ethyl group.

DETAILED DESCRIPTION

Tris(tri-sec-butoxysiloxy)methylsilane has the formula $CH_3-Si[OSi(O-sec-C_4H_9)_3]_3$. Methods for its preparation are described in U.S. Pat. Nos. 3,965,136 and 4,077,993, which are both incorporated herein by reference in their entireties.

Besides this alkoxysilane cluster compound, the organic phase of the emulsions of the present invention may contain organic waxes, oil, alcohols, polyethylene glycols, thickening agents, preservatives, dyes, and the like.

The aqueous phase of these emulsions may contain, besides water, inorganic salts, pH adjusters, thickening agents, preservatives, dyes, and the like.

The surfactants used to effect the emulsions of the present invention and their method of preparation are disclosed in U.S. Pat. No. 4,160,776, which issued to M. Scardera and D. Gavin on July 10, 1979, and is incorporated herein by reference in its entirety. Preferably, the use of about 10 moles to 14 moles of ethylene oxide (n=about 10 to about 14) per alkoxysilane group is desirable for even longer stability.

In the emulsion system of this invention, the above-noted surfactants may generally be employed in an amount from about 0.5% by weight to about 10% by weight, preferably from about 2% to about 6%, based on the total weight of the aqueous and organic phases of the emulsion.

The ratio of the aqueous phase to the organic phase may vary between about 10:1 to about 1:10 on a weight basis with the preferred range being from about 8:2 to about 2:8.

The following examples are further illustrative of this invention. All parts and percentages are by weight unless explicitly stated otherwise.

EXAMPLE 1

Preparation of Methoxy-Ethoxy (12.4)-Bis-(Tri-Sec-Butoxysiloxy)-Methylsilane

Step 1—Polyether Formation

A 500 ml. round bottom flask containing a magnetic stirring bar was fitted with a thermometer, graduated dropping funnel, nitrogen purge and dry ice condenser. The flask contained 93.14 g (0.242 mole) polyethylene glycol (8) mono-methyl ether and 0.2 g potassium hydroxide as catalyst. Under a nitrogen atmosphere, ethylene oxide, 46.9 g (1.07 moles) was added dropwise via the dropping funnel to the glycol ether at 140°–165° C. with stirring. Upon completion of the ethylene oxide addition, the reaction product was cooled and weighed—product weight 140 g (the methylethylene oxide ratio was 1:12.4 and molecular weight was 579 by hydroxyl number analysis).

Step 2—Surfactant Formation

In a 3-necked round bottom flask containing a magnetic stirring bar was placed 14.4 g (0.0248 mole) glycol ether-ethylene oxide product from Example 1 (Step 1) 2.37 g (0.03 mole) pyridine and 50 ml xylene. The flask was fitted with a thermometer, dropping funnel, and an air condenser. Bis(tri-sec-butoxysiloxy)-methylchlorosilane, 15.14 g (0.025 mole) and 50 ml xylene were mixed, placed in the dropping funnel, and gradually added to the contents of the flask with stirring at ambient temperature. Upon reaction, the white pyridine-HCl salt formed. Addition was complete in one hour, the temperature raised to 70°–80° C. and heated an additional hour to insure complete reaction. The reaction mixture was cooled to ambient temperature, the salt filtered off, and the clear filtrate placed on a rotary evaporator and heated to 80° C. under vacuum to insure removal of the excess pyridine and xylene solvent. The product was cooled and weighed. Product weight of the bis(tri-sec-butoxysiloxy)-methylsilane-(12.4 mole ethoxy)methyl adduct was 30 g.

EXAMPLE 2

Preparation of Ethoxy-Ethoxy (11)-Bis(Tri-Sec-Butoxysiloxy)-Methylsilane

The same procedure was followed as in Example 1 except:

Step 1—Polyether Formation

Employed 45 g (0.33 mole) diethylene glycol monoethyl ether and added 147 (3.34 moles) ethylene oxide. Product obtained was 191 g and the ethyl-ethylene oxide ratio was 1:11 with a molecular weight of 530 by hydroxyl number analysis.

Step 2—Surfactant Formation

Employed 13.25 g (0.025 mole) glycol ether-ethylene oxide product from Example 2 (Step 1), 2.2 g (0.028 mole) pyridine and 50 ml toluene. Added 15.13 g (0.025 mole) bis(tri-sec-butoxysiloxy)-methylchlorosilane in 50 ml toluene to the glycol. Product weight of the bis(tri-sec-butoxysiloxy)-methylsilane-(11 mole ethoxy)ethyl adduct was 27.4 g.

EXAMPLE 3

Preparation of Methoxy-Ethoxy (16)-Bis(Tri-Sec-Butoxysiloxy)-Methylsilane

The same procedure was followed as in Example 1 except:

Step 1—Polyether Formation

Employed 70 g (0.125 moles) polyethylene glycol (12) mono-methyl ether and added 22.35 g (0.51 mole) ethylene oxide. Product obtained was 92 g and the methyl-ethylene oxide ratio was 1:16 with a molecular weight of 757 by hydroxyl number analysis.

Step 2—Surfactant Formation

Employed 18.92 g (0.025 mole) glycol ether-ethylene oxide product from Example 3 (Step 1), 2.37 g (0.03 mole) pyridine and 50 ml xylene. Added 15.14 (0.025 mole) bis(tri-sec-butoxysiloxy)-methylchlorosilane in 50 ml xylene to the glycol. Product weight of the bis(tri-sec-butoxysiloxy)-methylsilane-(16 mole ethoxy)methyl adduct was 33.2 g.

EXAMPLES A TO I

Preparation of Emulsions Using Surfactant Prepared in Examples 1-3

In nine 100 ml beakers containing a weighed amount (8 to 32 g) of tris(tri-sec-butoxysiloxy) methylsilane (sometimes hereinafter referred to as SC-102) is added 1.6 g of the silicate surfactants from Examples 1-3. These mixtures are then poured into 50 ml emulsion tubes containing a weighed (32 to 8 g) amount of water. The emulsion tubes with their contents are stoppered and shaken for at least 30 seconds each. The emulsion tubes are then placed in an Atlab Emulsion Viewer and the stability of the emulsions measured by the length of time until "creaming" or breaking of the emulsion occurs—the longer the time, the greater the stability of the emulsion system. The results of these emulsion systems are given in Tables 1, 2, and 3.

TABLE 1

SC-102/WATER EMULSIONS
SURFACTANT: METHOXY-ETHOXY(12.4)-BIS(TRI-SEC-BUTOXYSILOXY)-METHYLSILANE

| EMULSION | A | B | C | D | E |
|---|---|---|---|---|---|
| SC-102 (g) | 8 | 16 | 20 | 24 | 32 |
| WATER (g) | 32 | 24 | 20 | 16 | 8 |
| SURFACTANT (g) | 1.6 | 1.6 | 1.6 | 1.6 | 1.6 |
| SC-102/WATER RATIO | 20/80 | 40/60 | 50/50 | 60/40 | 80/20 |
| EMULSION STABILITY (HRS) | 1.5 | >72 | >72 | >72 | >72 |

TABLE 2

SC-102/WATER EMULSIONS
SURFACTANT: ETHOXY-ETHOXY(11)-BIS(TRI-SEC-BUTOXYSILOXY)-METHYLSILANE

| EMULSION | F | G | H |
|---|---|---|---|
| SC-102 (g) | 16 | 24 | 32 |
| WATER (g) | 24 | 16 | 8 |
| SURFACTANT (g) | 1.6 | 1.6 | 1.6 |
| SC-102/WATER RATIO | 40/60 | 60/40 | 80/20 |
| EMULSION STABILITY (HRS) | >24 | >24 | >24 |

TABLE 3

SC-102/WATER EMULSIONS
SURFACTANT: METHOXY-ETHOXY(16)-BIS(TRI-SEC-BUTOXYSILOXY)-METHYLSILANE

| EMULSION | I |
|---|---|
| SC-102 (g) | 32 |
| WATER (g) | 8 |
| SURFACTANT (g) | 1.6 |
| SC-102/WATER RATIO | 80/20 |
| EMULSION STABILITY (HRS) | >48 |

EXAMPLE J

Treating Floor Tile With Emulsion B

These emulsions can be used in treating floor tile to restore luster either alone, or with added ingredients such as waxes or linseed oil. For example, the reflectance of floor tile was measured on a Hunterlab Reflectometer as "new", "worn (after steel wool abrasion)", and after treatment with Emulsion B—the higher the reflectance, the greater the luster. The following results were obtained:

| | REFLECTANCE |
|---|---|
| "New" Floor Tile | 44.2 |
| "Worn" Floor Tile | 35.1 |
| Emulsion B Treated Floor Tile | 39.6 |

COMPARISONS 1 AND 2

Preparation of emulsions employing methoxy-ethoxy(4)-bis(tri-sec-butoxysiloxy)methylsilane and methoxy-ethoxy(21)-bis(tri-sec-butoxysiloxy)methylsilane were stable for less than one hour. This data is shown in Table 4.

COMPARISONS 3A-3E

Preparation of emulsions employing nonylphenol-4.5 moles ethylene oxide adduct as the surfactant were stable for less than 20 minutes. This data is shown in Table 5.

COMPARISONS 4A-4E

Preparation of emulsions employing nonylphenol-9 moles ethylene oxide adduct as the surfactant were stable for less than one hour. This data is shown in Table 6.

COMPARISONS 5A-5E

Preparation of emulsions employing sodium dodecylbenzene sulfonate as the surfactant exhibited essentially no emulsion stability. This data is shown in Table 7.

COMPARISONS 6A–6C

Preparation of emulsions employing Dow Corning 544[1] as the surfactant were stable for less than 10 minutes. This data is shown in Table 8.

[1] A silicon based surfactant, product of Dow Corning Corp., Midland, Mich.

TABLE 4
SC-102/WATER EMULSIONS

| SURFACTANTS: COMPARISON | METHOXY-ETHOXY(4)BIS-(TRI-SEC-BUTOXYSILOXY)-METHYLSILANE 1 | METHOXY-ETHOXY(21)BIS-(TRI-SEC-BUTOXYSILOXY)-METHYLSILANE 2 |
|---|---|---|
| SC-102 (g) | 32 | 32 |
| WATER (g) | 8 | 8 |
| SURFACTANT (g) | 1.6 | 1.6 |
| SC-102/WATER RATIO | 80/20 | 80/20 |
| EMULSION STABILITY (HRS) | <1 | <1 |

TABLE 5
SC-102/WATER EMULSIONS
SURFACTANT: NONYLPHENOL - 4.5 MOLES ETHYLENE OXIDE

| COMPARISON | 3A | 3B | 3C | 3D | 3E |
|---|---|---|---|---|---|
| SC-102 (g) | 8 | 16 | 20 | 24 | 32 |
| WATER (g) | 32 | 24 | 20 | 16 | 8 |
| SURFACTANT (g) | 1.6 | 1.6 | 1.6 | 1.6 | 1.6 |
| SC-102/WATER RATIO | 20/80 | 40/60 | 50/50 | 60/40 | 80/20 |
| EMULSION STABILITY (MIN) | <1 | <1 | <1 | <20 | <20 |

TABLE 6
SC-102/WATER EMULSIONS
SURFACTANT: NONYLPHENOL - 9 MOLES ETHYLENE OXIDE

| COMPARISON | 4A | 4B | 4C | 4D | 4E |
|---|---|---|---|---|---|
| SC-102 (g) | 8 | 16 | 20 | 24 | 32 |
| WATER (g) | 32 | 24 | 20 | 16 | 8 |
| SURFACTANT (g) | 1.6 | 1.6 | 1.6 | 1.6 | 1.6 |
| SC-102/WATER RATIO | 20/80 | 40/60 | 50/50 | 60/40 | 80/20 |
| EMULSION STABILITY (MIN) | <2 | <4 | <6 | <60 | <40 |

TABLE 7
SC-102/WATER EMULSIONS
SURFACTANT: SODIUM DODECYLBENZENE SULFONATE

| COMPARISON | 5A | 5B | 5C | 5D | 5E |
|---|---|---|---|---|---|
| SC-102 (g) | 8 | 16 | 20 | 24 | 32 |
| WATER (g) | 32 | 24 | 20 | 16 | 8 |
| SURFACTANT (g) | 1.6 | 1.6 | 1.6 | 1.6 | 1.6 |
| SC-102/WATER RATIO | 20/80 | 40/60 | 50/50 | 60/40 | 80/20 |
| EMULSION STABILITY (MIN) | <1 | <1 | <1 | <1 | <1 |

TABLE 8
SC-102/WATER EMULSIONS
SURFACTANT: DOW CORNING 544 (SILICON SURFACTANT)

| COMPARISON | 6A | 6B | 6C |
|---|---|---|---|
| SC-102 (g) | 16 | 20 | 24 |
| WATER (g) | 24 | 20 | 16 |
| SURFACTANT (g) | 1.6 | 1.6 | 1.6 |
| SC-102/WATER RATIO | 40/60 | 50/50 | 60/40 |
| EMULSION STABILITY (MIN) | <9 | <8 | <2 |

What is claimed is:

1. A stable emulsion system comprising:
   (a) an aqueous phase comprising water;
   (b) an organic phase comprising tris(tri-sec-butoxysiloxy)methylsilane; and
   (c) a surfactant having the formula:

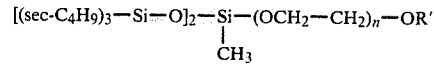

wherein n is from about 8 to 16 and R' is either a methyl or ethyl group.

2. The emulsion system of claim 1 wherein n is from about 10 to about 14.

3. The emulsion system of claim 1 wherein R' is methyl.

4. The emulsion system of claim 1 wherein R' is ethyl.

5. The emulsion system of claim 1 wherein the amount of said surfactant is from about 0.5% by weight to about 10% by weight of the total weight of the combined aqueous and organic phases.

6. The emulsion system of claim 1 wherein the weight ratio of the aqueous phase to the organic phase is from about 10:1 to about 1:10.

7. The emulsion system of claim 1 wherein the amount of said surfactant is from about 2% by weight to about 6% by weight of the total weight of the combined aqueous and organic phases.

8. The emulsion system of claim 7 wherein the weight ratio of the aqueous phase to the organic phase is from about 8:2 to 2:8.

9. The emulsion system of claim 8 wherein n is from about 10 to about 14 and R' is methyl.

10. The emulsion system of claim 8 wherein n is from about 10 to about 14 and R' is ethyl.

* * * * *